(12) United States Patent
Axelson, Jr. et al.

(10) Patent No.: US 7,628,817 B1
(45) Date of Patent: Dec. 8, 2009

(54) SOFT TISSUE DEFLECTION AT A PROSTHETIC JOINT

(75) Inventors: Stuart L. Axelson, Jr., Succasunna, NJ (US); Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 11/610,722

(22) Filed: Dec. 14, 2006

(51) Int. Cl.
*A61F 2/38* (2006.01)

(52) U.S. Cl. ................................. 623/20.14; 623/20.21

(58) Field of Classification Search .... 623/20.14–20.36
See application file for complete search history.

(56) References Cited

U.S. PATENT DOCUMENTS

| | | | |
|---|---|---|---|
| 4,178,641 A | 12/1979 | Grundei et al. | |
| 4,963,152 A | 10/1990 | Hofmann et al. | |
| 5,207,711 A | 5/1993 | Caspari et al. | |
| 5,413,605 A * | 5/1995 | Ashby et al. | 623/20.34 |
| 5,776,200 A | 7/1998 | Johnson et al. | |
| 5,879,396 A | 3/1999 | Walston et al. | |
| 6,197,064 B1 * | 3/2001 | Haines et al. | 623/20.31 |
| 6,342,075 B1 | 1/2002 | MacArthur | |
| 6,558,421 B1 | 5/2003 | Fell et al. | |
| 6,783,550 B2 | 8/2004 | MacArthur | |
| 6,855,165 B2 | 2/2005 | Fell et al. | |
| 2008/0009950 A1 * | 1/2008 | Richardson | 623/20.29 |

* cited by examiner

*Primary Examiner*—Corrine M McDermott
*Assistant Examiner*—Megan Wolf

(57) ABSTRACT

Where a prosthetic joint component part has a relatively sharp edge which potentially can contact and thereby irritate or injure soft tissue juxtaposed with the component part at an implant site during articulation of the prosthetic joint, such as a posterior cruciate ligament juxtaposed with a component part of a prosthetic knee, the component part is provided with a deflector located, configured, dimensioned and directed for deflecting the soft tissue away from contact with the sharp edge during articulation of the prosthetic joint.

13 Claims, 4 Drawing Sheets

SOFT TISSUE DEFLECTION AT A PROSTHETIC JOINT

BACKGROUND OF THE INVENTION

1. Field of the Invention

The present invention relates generally to prosthetic joints and pertains, more specifically, to an improvement in a prosthetic joint wherein component parts of the prosthetic joint are provided with structural features for deflecting surrounding soft tissue away from sharp edges which may be present at an implant site, during articulation of the prosthetic joint.

2. Description of the Related Prior Art

Prosthetic joints include component parts which are affixed to the natural bone at an implant site and which are held together by surrounding soft tissue for articulation of the component parts relative to one another. In a knee prosthesis, for example, a femoral component and a tibial component are held by collateral ligaments and by cruciate ligaments in an articulation relationship for appropriate flexion and extension of the knee prosthesis. Each component of the knee prosthesis is seated upon natural bone at the implant site, along a prepared area of a corresponding bone, the implant component being provided with a seating area for engaging the corresponding bone along the prepared area. The seating area is defined precisely by a relatively sharp peripheral edge so as to attain a desired well-seated engagement between the implant component and the prepared bone at the implant site. However, because of variations among recipients in the configuration of the natural bone at an implant site, a seated prosthetic implant component may extend beyond at least a portion of the peripheral boundary of the prepared area of the bone at the implant site, with the result that at least a portion of the sharp peripheral edge along the periphery of the seating surface will become exposed. These exposed sharp edges, if allowed to come into contact with soft tissue at the implant site, and especially a cruciate ligament during articulation of the prosthetic knee, can cause irritation of the ligament and eventual serious injury.

BRIEF SUMMARY OF THE INVENTION

The present improvement provides structural features in component parts of a prosthetic joint for addressing the above-outlined problem. As such, the present improvement attains several objects and advantages, some of which are summarized as follows: Provides a prosthetic joint with structural features which avoid deleterious effects that might otherwise arise as a result of contact between soft tissue and sharp edges at the implant site; avoids irritation and injury to soft tissue at the site of an implanted prosthetic joint, such as ligaments associated with a prosthetic knee, by deflecting the soft tissue away from sharp edges which may be present at the implant site; enables articulation of a prosthetic joint with increased ease and comfort, while avoiding irritation or injury to surrounding soft tissue; facilitates the implant of a prosthetic joint, such as a knee prosthesis, requiring less time to complete an accurate and effective implant procedure, with a concomitant decrease in patient recovery time; accomplishes an overall increase in the use and performance of a prosthetic joint without requiring a wide departure from proven current constructions and techniques; provides a prosthetic joint of improved construction, capable of exemplary performance over an extended service life.

The above objects and advantages, as well as further objects and advantages, are attained by the present invention which may be described briefly as an improvement in a component part of a prosthetic joint in which component parts are to be seated upon a prepared area of natural bone at an implant site and held in place relative to one another by surrounding soft tissue during articulation of the component parts, the prepared area having a peripheral boundary and the component part including a seating area for engaging the prepared area upon implant of the component part, the improvement wherein the component part includes: a peripheral edge for juxtaposition with the peripheral boundary of a corresponding prepared area upon placement of the component part at the implant site; and a deflector placed adjacent at least a portion of the peripheral edge for juxtaposition with soft tissue adjacent the portion of the peripheral edge upon seating of the component part at the implant site, the deflector being located, configured, dimensioned and directed for deflecting the juxtaposed soft tissue away from contact with the peripheral edge of the seating area during articulation of the prosthetic joint.

In addition, the present invention provides a method for protecting surrounding soft tissue against irritation or injury from contact with a component part of a prosthetic joint during articulation of the prosthetic joint in which component parts are seated upon a prepared area of natural bone at an implant site and held in place relative to one another by the surrounding soft tissue during articulation of the component parts, the prepared area having a peripheral boundary and the component part including a seating area for engaging the prepared area, the seating area including a peripheral edge, the method comprising: placing a deflector adjacent at least a portion of the peripheral edge, in juxtaposition with soft tissue adjacent the portion of the peripheral edge, the deflector being located, configured, directed and dimensioned for deflecting the juxtaposed soft tissue away from contact with the peripheral edge of the seating area during articulation of the prosthetic joint.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing in which.

DETAILED DESCRIPTION OF THE INVENTION

Figure 1:
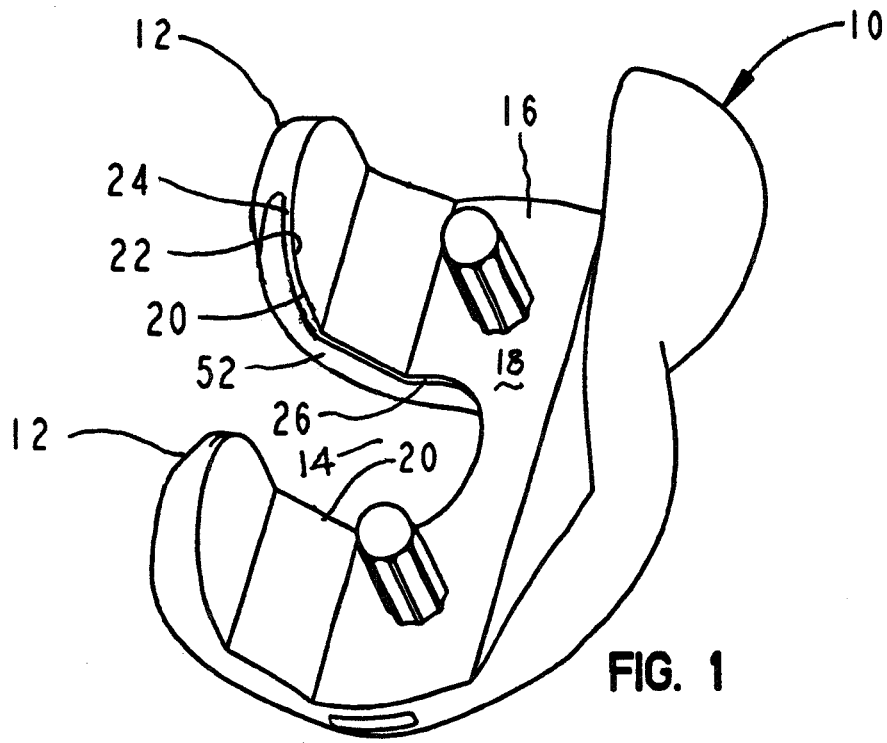
FIG. 1 is a pictorial view of a component part of a prosthetic knee implant illustrating an embodiment of the present invention.
Figure 2:
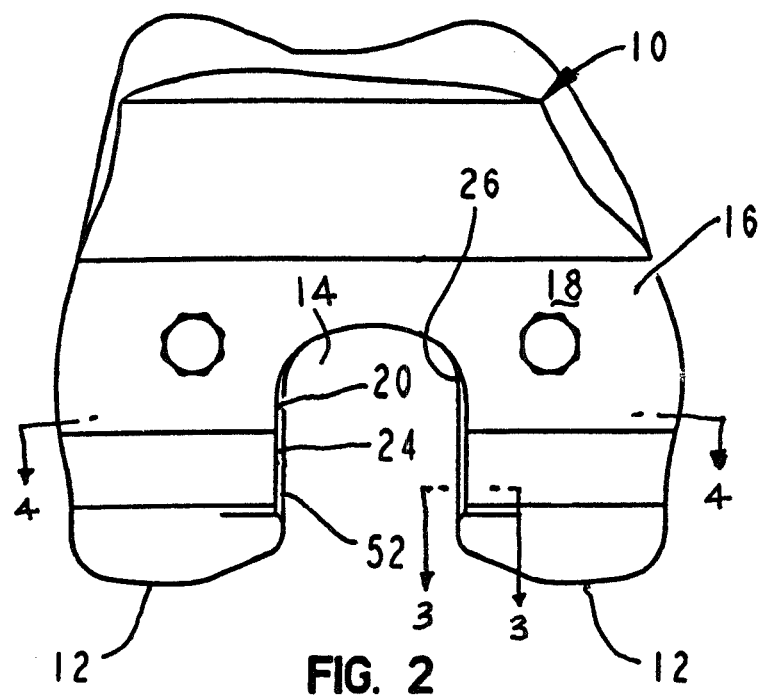
FIG. 2 is a top plan view of the component part.
Figure 3:
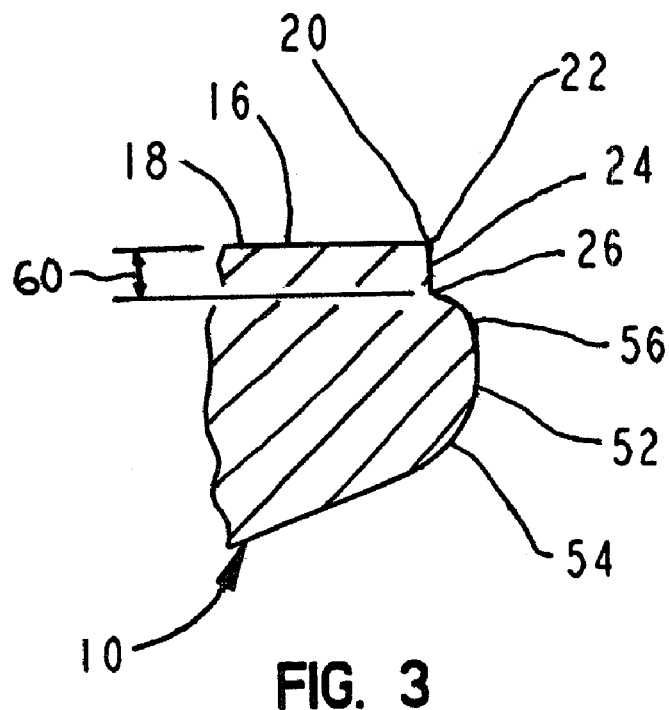
FIG. 3 is an enlarged fragmentary cross-sectional view taken along line 3-3 of FIG. 2.

Referring now to the drawing, and especially to FIG. 1 thereof, a component part of a prosthetic joint is shown in the form of a femoral component 10 of a total knee prosthesis. As is conventional in a total knee prosthesis, femoral component 10 includes condyles 12 spaced apart in a transverse direction by an intercondylar notch 14. A seating area 16 extends over superior surface 18 of the femoral component 10 for engaging a prepared area of natural bone at an implant site, as is now well-known in the art of prosthetic joints, and further as set forth in detail below. As best seen in FIGS. 2 and 3, as well as in FIG. 1, a peripheral edge 20 extends along the perimeter of the seating area 16 and presents a relatively sharp corner 22 at the perimeter of the seating area 16, particularly along a portion of the peripheral edge 20 which meets the wall 24 of the intercondylar notch 14 along border 26 of the intercondylar notch 14.

Figure 4:
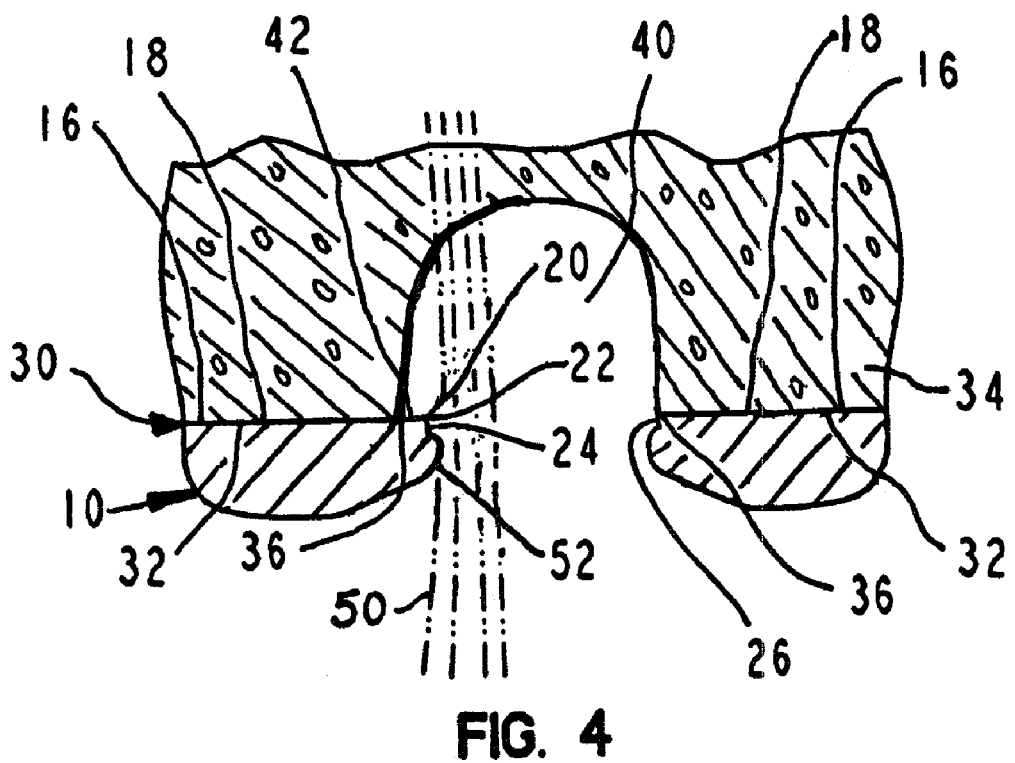
FIG. 4 is a cross-sectional view taken along line 4-4 of FIG. 2, with the component part in place at an implant site.

Turning to FIG. 4, as well as to FIGS. 1 through 3, upon placement of femoral component 10 at an implant site 30, seating area 16 is engaged with prepared area 32 of distal femur 34, placing peripheral edge 20 in juxtaposition with peripheral boundary 36 of prepared area 32. In order to attain a desired, well-seated engagement between femoral component 10 and the natural bone at distal femur 34, seating area 16 is defined precisely and is configured for engagement with prepared area 32 without deleterious gaps or voids, by virtue of the relatively sharp corner 22 provided at peripheral edge 20. However, because of variations among recipients of a prosthetic knee in the configuration of the natural bone available at the implant site of the prosthetic knee, and especially along the natural intercondylar notch, as illustrated by intercondylar notch 40 at implant site 30, upon placement of the femoral component 10 at the implant site 30 at least a portion of the peripheral edge 20 of the seating area 16 may extend beyond the peripheral boundary 36 of the prepared area 32 of the distal femur 34, resulting in the exposure of at least a portion of the sharp peripheral edge 20, especially along border 26 of the intercondylar notch 14 of the femoral component 10, as illustrated by portion 42 of peripheral edge 20, which portion 42 lies beyond the peripheral boundary 36 of prepared area 32, spaced in a transverse direction from an adjacent portion of the peripheral boundary 36 to expose the sharp corner 22 between superior surface 18 and wall 24 at the natural intercondylar notch 40.

Exposure of the sharp peripheral edge 20 creates a potential for irritation or injury to soft tissue in the vicinity of the exposed peripheral edge 20 through contact between the soft tissue and the exposed sharp peripheral edge 20 during articulation of the knee prosthesis, in this instance, the posterior cruciate ligament 50 present at the intercondylar notch 40 and juxtaposed with the exposed peripheral edge 20 of the femoral component 10. In order to avoid such soft tissue irritation or injury, femoral component 10 is provided with a deflector, shown in the form of protuberance 52, located, configured, dimensioned and directed for deflecting the juxtaposed posterior cruciate ligament 50 away from contact with peripheral edge 20 during articulation of the knee prosthesis.

Protuberance 52 extends along the intercondylar notch 14 of the femoral component 10, has a cross-sectional configuration directed in a transverse direction and projects transversely a sufficient distance into the intercondylar notch 14 to engage the juxtaposed posterior cruciate ligament 50 for diverting the juxtaposed posterior cruciate ligament 50 away from contact with peripheral edge 20 during articulation of the knee prosthesis, thus avoiding irritation or injury during articulation of the knee prosthesis. Further to that end, protuberance 52 is provided with a surface contour configuration which presents a smooth convex surface 54, preferably including an arcuate profile 56, that is, a profile which follows a symmetric or asymmetric curve, for engaging the posterior cruciate ligament 50. In order to preserve the sharp corner 22 of peripheral edge 20, as desired for effective seating of the seating area 16 upon the prepared area 32 of the distal femur 34, protuberance 52 is spaced from peripheral edge 20 in an inferior direction, as illustrated by spacing 60. In the preferred construction, illustrated in connection with femoral component 10 of a total knee prosthesis, protuberance 52 extends continuously along the entire perimeter of intercondylar notch 14 so as to be available to divert posterior cruciate ligament 50 away from contact with any portion of peripheral edge 20 which may become exposed.

Figure 5:
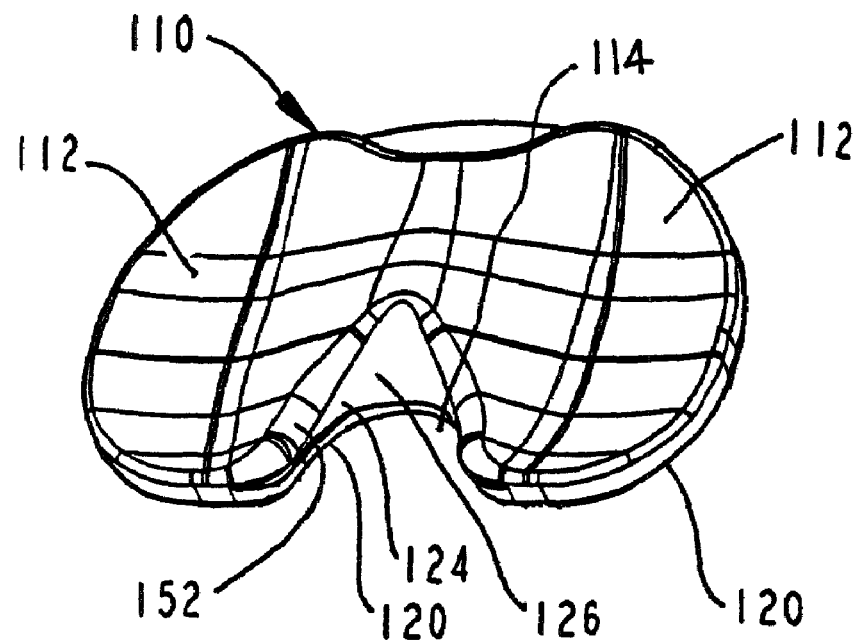
FIG. 5 is a pictorial view of another component part of a prosthetic knee implant illustrating another embodiment of the present invention.
Figure 6:
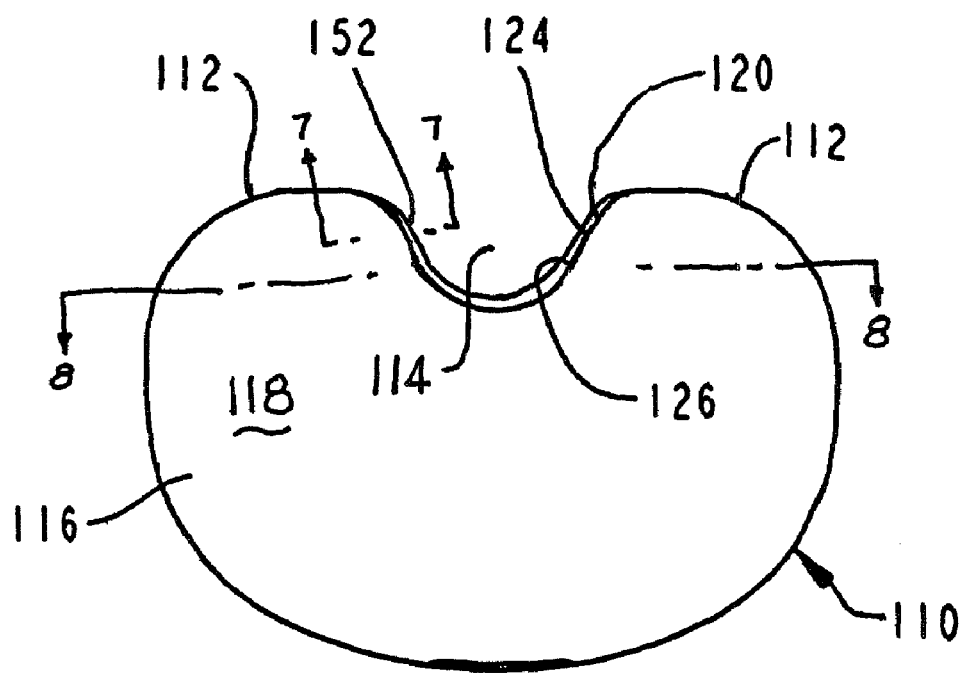
FIG. 6 is a bottom plan view of the component part of FIG. 5.
Figure 7:
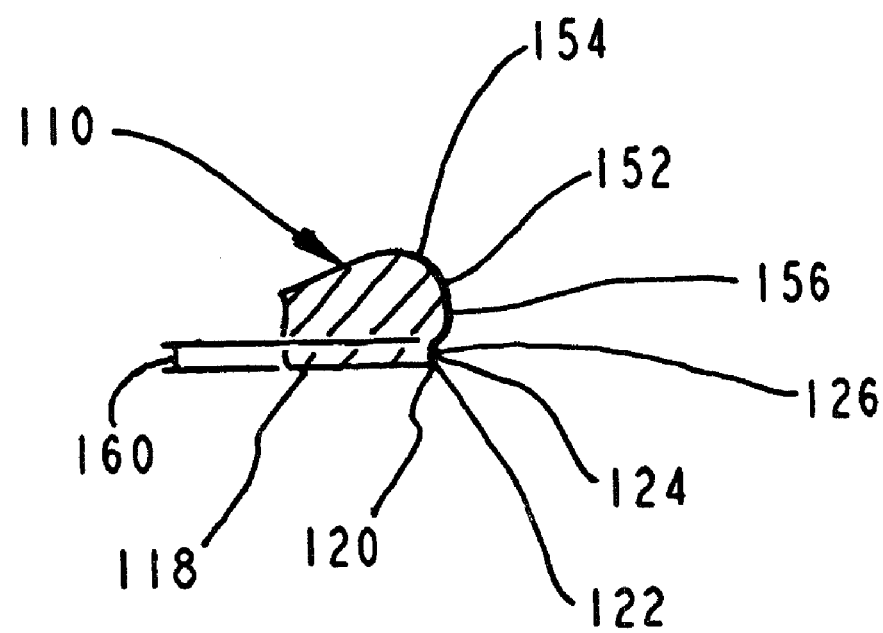
FIG. 7 is an enlarged fragmentary cross-sectional view taken along line 7-7 of FIG. 6.

In the embodiment illustrated in FIGS. 5 through 8, a component part of a prosthetic joint is shown in the form of a tibial component 110 of a total knee prosthesis. As is conventional in a total knee prosthesis, tibial component 110 includes articular surfaces 112 spaced apart in a transverse direction by an intercondylar notch 114. A seating area 116 extends over inferior surface 118 of the tibial component 110 for engaging a prepared area of natural bone at an implant site, as is now well-known in the art of prosthetic joints, and further as set forth in detail below. As best seen in FIGS. 6 and 7, as well as in FIG. 5, a peripheral edge 120 extends along the perimeter of the seating area 116 and presents a relatively sharp corner 122 at the perimeter of the seating area 116, particularly along a portion of the peripheral edge 120 which meets the wall 124 of the intercondylar notch 114 along border 126 of the intercondylar notch 114.

Figure 8:
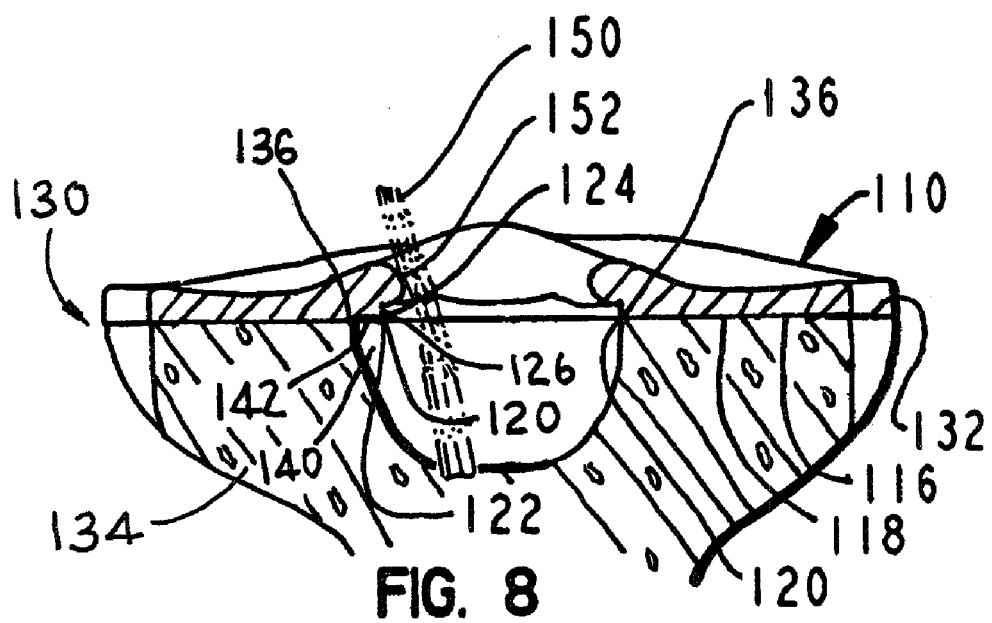
FIG. 8 is a cross-sectional view taken along line 8-8 of FIG. 6, with the component part in place at an implant site.

Turning to FIG. 8, as well as to FIGS. 5 through 7, upon placement of tibial component 110 at an implant site 130, seating area 116 is engaged with prepared area 132 of proximal tibia 134, placing peripheral edge 120 in juxtaposition with peripheral boundary 136 of prepared area 132. In order to attain a desired, well-seated engagement between tibial component 110 and the natural bone at proximal tibia 134, seating area 116 is defined precisely and is configured for engagement with prepared area 132 without deleterious gaps or voids, by virtue of the relatively sharp corner 122 provided at peripheral edge 120. However, because of variations among recipients of a prosthetic knee in the configuration of the natural bone available at the implant site of the prosthetic knee, and especially along the natural intercondylar notch, as illustrated by intercondylar notch 114 at implant site 130, upon placement of the tibial component 110 at the implant site 130, at least a portion of the peripheral edge 120 of the seating area 116 may extend beyond the peripheral boundary 136 of the prepared area 132 of the proximal tibia 134, resulting in the exposure of at least a portion of the sharp peripheral edge 120, especially along border 126 of the intercondylar notch 114 of the tibial component 110, as illustrated by portion 142 of peripheral edge 120, which portion 142 lies beyond the peripheral boundary 136 of prepared area 132, spaced in a transverse direction from an adjacent portion of the peripheral boundary 136 to expose the sharp corner 122 between superior surface 118 and wall 124 at the natural intercondylar notch 140.

Exposure of the sharp peripheral edge 120 creates a potential for irritation or injury to soft tissue in the vicinity of the exposed peripheral edge 120 through contact between the soft tissue and the exposed sharp peripheral edge 120 during articulation of the knee prosthesis, in this instance, the posterior cruciate ligament 150 present at the intercondylar notch 114 and juxtaposed with the exposed peripheral edge 120 of the tibial component 110. In order to avoid such soft tissue irritation or injury, tibial component 110 is provided with a deflector, shown in the form of protuberance 152, located, configured, dimensioned and directed for deflecting the juxtaposed posterior cruciate ligament 150 away from contact with peripheral edge 120 during articulation of the knee prosthesis.

Protuberance 152 extends along the intercondylar notch 114 of the tibial component 110, has a cross-sectional configuration directed in a transverse direction and projects transversely a sufficient distance into the intercondylar notch 114 to engage the juxtaposed posterior cruciate ligament 150 for diverting the juxtaposed posterior cruciate ligament 150 away from contact with peripheral edge 120 during articulation of the knee prosthesis, thus avoiding irritation or injury during articulation of the knee prosthesis. Further to that end, protuberance 152 is provided with a surface contour configuration which presents a smooth convex surface 154, preferably including an arcuate profile 156, that is, a profile which follows a symmetric or asymmetric curve, for engaging the posterior cruciate ligament 150. In order to preserve the sharp corner 122 of peripheral edge 120, as desired for effective seating of the seating area 116 upon the prepared area 132 of the proximal tibia 134, protuberance 152 is spaced from peripheral edge 120 in a superior direction, as illustrated by spacing 160. In the preferred construction, illustrated in connection with tibial component 110 of a total knee prosthesis, protuberance 152 extends continuously along the entire perimeter of intercondylar notch 114 so as to be available to divert posterior cruciate ligament 150 away from contact with any portion of peripheral edge 120 which may become exposed.

It will be seen that the present invention attains all of the objects and advantages summarized above; namely, Provides a prosthetic joint with structural features which avoid deleterious effects that might otherwise arise as a result of contact between soft tissue and sharp edges at the implant site; avoids irritation and injury to soft tissue at the site of an implanted prosthetic joint, such as ligaments associated with a prosthetic knee, by deflecting the soft tissue away from sharp edges which may be present at the implant site; enables articulation of a prosthetic joint with increased ease and comfort, while avoiding irritation or injury to surrounding soft tissue; facilitates the implant of a prosthetic joint, such as a knee prosthesis, requiring less time to complete an accurate and effective implant procedure, with a concomitant decrease in patient recovery time; accomplishes an overall increase in the use and performance of a prosthetic joint without requiring a wide departure from proven current constructions and techniques; provides a prosthetic joint of improved construction, capable of exemplary performance over an extended service life.

It is noted that while the illustrated embodiments are in the form of a femoral component and a tibial component of a total knee prosthesis, the present invention attains the same objects and advantages in femoral and tibial components of unicompartmental and bicompartmental knee prostheses.

It is to be understood that the above detailed description of preferred embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. An improvement in a component part of a prosthetic joint in which component parts are to be seated upon an area of natural bone at an implant site and held in place relative to one another by surrounding soft tissue extending in an anatomical direction for holding the component parts in place during articulation of the component parts, the area of natural bone having a peripheral boundary and the component part including a seating area for engaging the area of natural bone upon implant of the component part, the seating area having a perimeter, the improvement wherein the component part includes:
    a peripheral edge extending along the perimeter of the seating area for juxtaposition with the peripheral boundary of a corresponding area of natural bone upon placement of the component part at the implant site, the peripheral edge presenting a sharp corner along the perimeter of the seating area; and
    a deflector placed adjacent at least a portion of the sharp corner of the peripheral edge for juxtaposition with soft tissue adjacent the portion of the sharp corner of the peripheral edge upon seating of the component part at the implant site with the portion of the sharp corner of the peripheral edge spaced away from a corresponding portion of the peripheral boundary of the area of natural bone in a direction transverse to the anatomical direction such that the portion of the sharp corner is exposed with respect to the area of natural bone, the deflector being located, configured, dimensioned and directed for deflecting the juxtaposed soft tissue away from contact with the exposed portion of the sharp corner of the peripheral edge during articulation of the prosthetic joint;
    the deflector comprising a protuberance spaced away from the sharp corner of the peripheral edge along an inferior-superior direction and projecting in the transverse direction beyond the exposed portion of the sharp corner of the peripheral edge, the protuberance having a convex surface contour configuration providing a smooth surface for engaging the juxtaposed soft tissue to divert the juxtaposed soft tissue away from contact with the exposed portion of the sharp corner of the peripheral edge during articulation of the prosthetic joint.

2. The improvement of claim 1 wherein the surface contour configuration includes an arcuate profile.

3. The improvement of claim 1 wherein:
    the component part comprises a femoral component of a knee prosthesis, the femoral component having a border for being juxtaposed with a posterior cruciate ligament upon implant of the femoral component at the implant site;
    the seating area extends along a superior surface of the femoral component;
    the sharp corner of the peripheral edge extends along at least a portion of the border of the femoral component at a corresponding portion of the superior surface; and
    the protuberance extends along the border of the femoral component and is spaced away from the sharp corner of the peripheral edge in an inferior direction, thereby placing the protuberance in position for juxtaposition with the posterior cruciate ligament, upon seating of the femoral component at the implant site, for engaging the juxtaposed posterior cruciate ligament to divert the posterior cruciate ligament away from contact with the exposed portion of the sharp corner of the peripheral edge during articulation of the knee prosthesis.

4. The improvement of claim 3 wherein the surface contour configuration includes an arcuate profile.

5. The improvement of claim 1 wherein:
    the component part comprises a femoral component of a total knee prosthesis, the femoral component having an intercondylar notch for being juxtaposed with a posterior cruciate ligament upon implant of the femoral component at the implant site;

the seating area extends along a superior surface of the femoral component;

the sharp corner of the peripheral edge extends along at least a portion of the intercondylar notch at a corresponding portion of the superior surface; and the protuberance extends along the intercondylar notch and is spaced away from the sharp corner of the peripheral edge in an inferior direction, thereby placing the protuberance in position for juxtaposition with the posterior cruciate ligament, upon seating of the femoral component at the implant site, for engaging the juxtaposed posterior cruciate ligament to divert the posterior cruciate ligament away from contact with the exposed portion of the sharp corner of the peripheral edge during articulation of the knee prosthesis.

6. The improvement of claim 5 wherein the surface contour configuration includes an arcuate profile.

7. The improvement of claim 1 wherein:

the component part comprises a tibial component of a knee prosthesis, the tibial component having a border for being juxtaposed with a posterior cruciate ligament upon implant of the tibial component at the implant site;

the seating area extends along an inferior surface of the tibial component;

the sharp corner of the peripheral edge extends along at least a portion of the border of the tibial component at a corresponding portion of the inferior surface; and the protuberance extends along the border of the tibial component and is spaced away from the sharp corner of the peripheral edge in a superior direction, thereby placing the protuberance in position for juxtaposition with the posterior cruciate ligament, upon seating of the tibial component at the implant site, for engaging the juxtaposed posterior cruciate ligament to divert the posterior cruciate ligament away from contact with the exposed portion of the sharp corner of the peripheral edge during articulation of the knee prosthesis.

8. The improvement of claim 7 wherein the surface contour configuration includes an arcuate profile.

9. The improvement of claim 1 wherein:

the component part comprises a tibial component of a total knee prosthesis, the tibial component having an intercondylar notch for being juxtaposed with a posterior cruciate ligament upon implant of the tibial component at the implant site;

the seating area extends along an inferior surface of the tibial component;

the sharp corner of the peripheral edge extends along at least a portion of the intercondylar notch at a corresponding portion of the inferior surface; and the protuberance extends along the intercondylar notch and is spaced away from the sharp corner of the peripheral edge in a superior direction, thereby placing the protuberance in position for juxtaposition with the posterior cruciate ligament, upon seating of the tibial component at the implant site, for engaging the juxtaposed posterior cruciate ligament to divert the posterior cruciate ligament away from contact with the exposed portion of the sharp corner of the peripheral edge during articulation of the knee prosthesis.

10. The improvement of claim 9 wherein the surface contour configuration includes an arcuate profile.

11. A method for protecting surrounding soft tissue against irritation or injury from contact with a component part of a prosthetic joint during articulation of the prosthetic joint in which component parts are seated upon an area of natural bone at an implant site and held in place relative to one another by the surrounding soft tissue during articulation of the component parts, the surrounding soft tissue extending in an anatomical direction, the area of natural bone having a peripheral boundary and the component part including a seating area for engaging the area of natural bone, the seating area having a perimeter and including a peripheral edge presenting a sharp corner along the perimeter of the seating area, the method comprising:

placing a protuberance adjacent at least a portion of the sharp corner of the peripheral edge, in juxtaposition with soft tissue adjacent the portion of the sharp corner of the peripheral edge upon seating of the component part at the implant site with the portion of the sharp corner of the peripheral edge spaced away from a corresponding portion of the peripheral boundary of the area of natural bone in a direction transverse to the anatomical direction such that the portion of the sharp corner is exposed with respect the area of natural bone, and with the protuberance spaced away from the exposed portion of the sharp corner of the peripheral edge along an inferior/superior direction and projecting in the transverse direction beyond the exposed portion of the sharp corner of the peripheral edge, thereby placing the protuberance in position for engaging the juxtaposed soft tissue to divert the juxtaposed soft tissue away from contact with the exposed portion of the sharp corner of the peripheral edge of the seating area during articulation of the prosthetic joint.

12. The method of claim 11 wherein the prosthetic joint is a knee prosthesis, the component part is a femoral component of the knee prosthesis, the soft tissue comprises a posterior cruciate ligament, and the protuberance is spaced away from the sharp corner of the peripheral edge in an inferior direction, thereby placing the protuberance in position for engaging the juxtaposed posterior cruciate ligament to divert the juxtaposed posterior cruciate ligament away from contact with the exposed portion of the sharp corner of the peripheral edge of the seating area during articulation of the knee prosthesis.

13. The method of claim 11 wherein the prosthetic joint is a knee prosthesis, the component part is a tibial component of the knee prosthesis, the soft tissue comprises a posterior cruciate ligament, and the protuberance is spaced away from the sharp corner of the peripheral edge in a superior direction, thereby placing the protuberance in position for engaging the juxtaposed posterior cruciate ligament to divert the juxtaposed posterior cruciate ligament away from contact with the exposed portion of the sharp corner of the peripheral edge of the seating area during articulation of the knee prosthesis.

* * * * *